US 6,747,268 B1

(12) United States Patent
Ume

(10) Patent No.: US 6,747,268 B1
(45) Date of Patent: Jun. 8, 2004

(54) OBJECT INSPECTION METHOD AND SYSTEM

(75) Inventor: Ifeanyi Charles Ume, Atlanta, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 09/541,571

(22) Filed: Apr. 3, 2000

Related U.S. Application Data

(60) Provisional application No. 60/127,664, filed on Apr. 2, 1999.

(51) Int. Cl.$^7$ .................................................. G01J 1/04
(52) U.S. Cl. ...................... 250/227.11; 73/627; 73/628; 702/35; 702/40
(58) Field of Search .................. 250/227.11, 559.22, 250/559.4; 359/702; 702/35, 40; 356/493, 494; 73/627, 628, 653, 655, 661

(56) References Cited

U.S. PATENT DOCUMENTS

| 4,246,793 A | * | 1/1981 | Fairand et al. ................. 73/628 |
| 4,756,696 A | | 7/1988 | Whiteman, Jr. ............... 439/79 |
| 4,876,455 A | * | 10/1989 | Sanderson et al. ........... 250/560 |
| 4,967,152 A | * | 10/1990 | Patterson ..................... 324/752 |
| 5,099,693 A | * | 3/1992 | Payne et al. ................... 73/632 |
| 5,190,163 A | * | 3/1993 | Anzai et al. ................. 209/588 |
| 5,457,997 A | | 10/1995 | Naruo et al. ................... 73/643 |
| 5,585,921 A | | 12/1996 | Pepper et al. ................ 356/357 |
| 5,604,592 A | * | 2/1997 | Kotidis et al. ............... 356/493 |
| 5,629,865 A | * | 5/1997 | Roth ............................. 702/56 |
| 5,760,904 A | * | 6/1998 | Lorraine et al. ............ 356/513 |
| 5,966,020 A | | 10/1999 | Rampone et al. ............ 324/755 |
| 6,181,431 B1 | * | 1/2001 | Siu .............................. 356/502 |

OTHER PUBLICATIONS

T.D. Dudderar, B.R. Peters, J.A. Gilbert, "Fiber Optic Sensor Systems for Ultrasonic NDE: State of the Art and Future Potential," IEEE 1989 Ultrasonics Symposium (Oct. 3–6); pp 1181–1189.*

Dudderar et al. (1989), "Fiber Optic Sensor Systems for Ultrasonic NDE: State of the Art and Future Potential," IEEE 1989 UltraSonics (Oct. 3–6); pp 1181–1189.*

Sandra N. Hopko, "Laser Ultrasonic Probe for Industrial or High Temperature Applications," Sep. 1998.

Sheng Liu, Dathan Erdahl and I. Charles Ume, "A Novel Method and Device for Solder Quality Inspection by Using Laser Ultrasound".

Sheng Liu, Dathan Erdahl and I. Charles Ume, "A Novel Approach for Solder Joint Quality Inspection: Laser Ultrasound and Interferometric System".

Sandra N. Hopko, "Laser Ultrasonic Probe for Industrial or High Temperature Applications," Sep., 1998 C. B Scruby, L.E. Drain, "Laser Ultrasonics, Techniques and Applications,".

Abstract of Laser Ultrasonic of Solder Connection in Integrated Chips, J. Acoust. Soc. Am., vol. 100, No. 4, Pt. 2, Oct. 1996, p. 2775.

* cited by examiner

Primary Examiner—David V. Bruce
Assistant Examiner—Courtney Thomas
(74) Attorney, Agent, or Firm—Thomas, Kayden, Horstemeyer & Risley, LLP

(57) ABSTRACT

The present disclosure relates to an object inspection system. The object inspection system comprises an ultrasound source capable of exciting the object to be tested with a stimulus such that the object vibrates at an ultrasound frequency, at least one optical fiber optically connected to the ultrasound source and adapted to be positioned with its exit end in close proximity to a surface of the object to be tested to deliver the stimulus to the object, a vibration sensing device adapted to sense the ultrasonic vibration displacements created in the object by the ultrasound source, and a system controller which receives the ultrasonic vibration data from the vibration sensing device. In a preferred arrangement, the object inspection system comprises a solder joint inspection system for testing the integrity of solder joints used to connect a computer chip to a printed circuit board.

27 Claims, 6 Drawing Sheets

OBJECT INSPECTION METHOD AND SYSTEM

The present application claims the benefit of the filing date of U.S. Provisional Patent Application Serial No. 60/127,664, filed on Apr. 2, 1999, which is hereby incorporated by reference.

FIELD OF THE INVENTION

The present disclosure relates to an object inspection method and system. More particularly, the disclosure relates to a solder joint quality inspection system particularly useful for inspecting solder bumps or balls which is non-contact, non-destructive, and which can be used either during process development or during on-line manufacturing.

BACKGROUND OF THE INVENTION

Computer chips are connected to computer boards, such as printed circuit boards (PCB's), normally by soldering. For instance, conventional computer chips have been connected to such boards in the past by soldering a plurality of pins extending from the chip to the board. Presently, consumer demands are driving the current trend in the electronics industry to make products that are compact, high in density, light, and thin. These demands have created new chip interconnection methods. One such interconnection method is known as solder bump or ball technology. Flip chip, ball grid arrays, chip scales, and multi-chip modules each use small solder bumps underneath the chips for interconnection, making them superior in performance to other more conventional interconnection technologies.

Solder joint quality inspection for traditional interconnection technologies typically comprise visual inspection techniques. Unfortunately, visual inspection techniques are ineffective for inspecting solder bumps because these bumps are hidden from view when used to connect a chip to a board. Moreover, these techniques are unsuitable for on-line inspection in that they require a large amount of time and are susceptible to human error. Therefore, new techniques for detecting flip chip and BGA solder joint defects are needed.

Currently, there are three main techniques used to inspect the solder joint quality of solder bump connected chips. These include x-ray detection methods, acoustic microscopy, and functional testing methods. There are two main types of x-ray detection methods: laminography and microfocus radiography. The difference between these two hinges mainly on cost, complexity, and shadowing. Although x-ray laminography can produce images of cross-sections of a solder joint, it is cost prohibitive and time consuming. The x-ray radiography approach provides a means of looking through the chips and substrates to see the relative location and size of the solder bumps. However, because this method relies on changes in the thickness of the material through which the x-rays pass, poor connections, delaminations, and cracks are very difficult to detect. In addition, the images which are produced by this technique must be correctly interpreted. Extracting solder joint quality information from these images, is difficult, time consuming, and subjective, making the process difficult to automate.

Acoustic microscopes utilize high-frequency ultrasound to examine the internal features in materials and components. Defects such as preexisting voids or non-wet conditions can be observed. However, the ultrasonic imaging systems currently available in the market are destructive techniques because the board assembly must be immersed in water during the inspection process. As can be appreciated, this technique is also too slow for on-line inspection, normally requiring several minutes to image the solder bumps under each single chip. Because many solder joints are located near the edge of the chip, edge effects can distort the ultrasound, providing a poor image in the region of interest.

The most widely used on-line inspection techniques are functional testing methods, such as the flying probe or the bed of nails methods. In these techniques, a test fixture checks for electrical continuity and proper operation of the assembled board by comparing the electrical response at specific nodes of the board to previously determined values. However, unsoldered joints may still pass this test if mechanical contact exists, even though the joint may fail after a short service life because of cracks or partial connections.

From the foregoing, it can be appreciated that it would be desirable to have an on-line, high resolution, fast, low cost, non-contact, and non-destructive method and system for inspecting solder joint quality.

SUMMARY OF THE INVENTION

The present disclosure relates to an object inspection system. The object inspection system comprises an ultrasound source capable of exciting the object to be tested with a stimulus such that the object vibrates at an ultrasound frequency, at least one optical fiber optically connected to the ultrasound source and adapted to be positioned with its exit end in close proximity to a surface of the object to be tested, the at least one optical fiber delivering the stimulus to the object, a vibration sensing device adapted to sense the ultrasonic vibration displacements created in the object with the ultrasound source, and a system controller which receives the ultrasonic vibration data from the vibration sensing device.

In a preferred arrangement, the object inspection system comprises a solder joint inspection system for testing the integrity of solder joints used to connect a computer chip to a printed circuit board. When arranged as a solder joint inspection system, the system can comprise a laser capable of producing a pulsed laser beam used to excite the object to be tested such that the object vibrates at an ultrasound frequency, at least one optical fiber optically connected to the laser and adapted to be positioned with its exit end in close proximity to a surface of the object to be tested, the at least one optical fiber delivering at least a fraction of the pulsed laser beam to the object, a laser interferometer adapted to sense the ultrasonic vibration displacements created in the object with the ultrasound source, and logic configured to process the ultrasonic vibration data used to evaluate the object.

The present disclosure also relates to a method for inspecting an object that comprises exciting the object with a pulsed laser beam such that it vibrates at an ultrasonic frequency, the pulsed laser beam being delivered to a surface of the object with at least one optical fiber, sensing the vibrations of the object to obtain vibration displacement data at a plurality of discrete, predetermined points of the object and processing the vibration displacement data and comparing it to vibration displacement data of a non-defective object to determine whether the tested object is defective.

The features and advantages of the invention will become apparent upon reading the following specification, when taken in conjunction with the accompanying drawings.

BRIEF DESCRIPTION OF THE DRAWINGS

The invention can be better understood with reference to the following drawings. The components in the drawings are not necessarily to scale, emphasis instead being placed upon clearly illustrating the principles of the present invention.

DETAILED DESCRIPTION

System Apparatus

Figure 1:
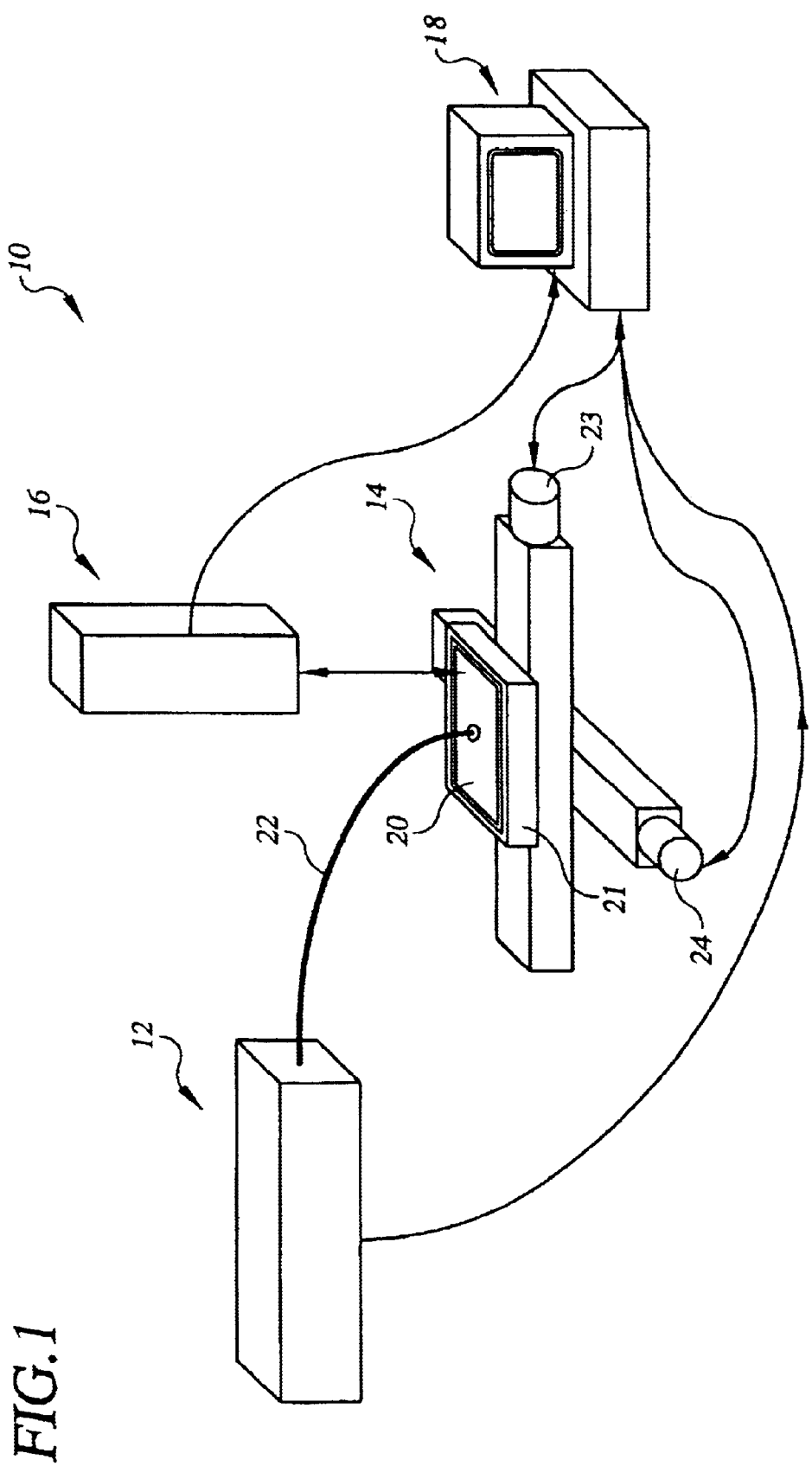
FIG. 1 is a schematic representation of a solder joint quality inspection system constructed in accordance with the principles of the present invention.

Referring now in more detail to the drawings, in which like numerals indicate corresponding parts throughout the several views, FIG. 1 illustrates an object inspection system 10 constructed in accordance with the principles of the present invention. As indicated in this figure, the system 10 generally comprises an ultrasound source 12, a positioning system 14, a vibration sensing device 16, and a system controller 18. In a preferred arrangement, the ultrasound source 12 comprises a laser. By way of example, this laser can comprise a Q-switched Nd-YAG laser, having a wavelength of approximately 1064 $\mu$m. As is discussed in more detail below, the ultrasound source 12 can be used to excite a chip 20 that is mounted to a board 21, such as a printed circuit board, which is disposed on the positioning system 14. Preferably, a laser beam produced by the ultrasound source 12 is directed toward the surface of the chip 20 with one or more optical fibers 22. By way of example, the optical fiber 22 can have a core diameter of approximately 1 mm. As shown in FIG. 1, the exit end of the optical fiber 22 will be positioned in close proximity to the chip 20 in that the laser energy provided by the ultrasound source 12 diverges rapidly after leaving the fiber 22. To provide space for the measurements performed by the vibration sensing device 16, the fiber 22 normally is oriented such that it approaches the chip 20 at an angle of approximately 45°. This angulation also prevents reflected laser pulses from damaging the vibration sensing device 16. Although a bare laser beam can be used to excite the chip 20, the use of an optical fiber 22 or fibers is advantageous in that it provides a flexible coupling between the ultrasound source 12 and the chip 20. Accordingly, the ultrasound source 12 can be positioned remotely from the remainder of the test apparatus which greatly simplifies the system, reducing costs considerably. Using fibers to transmit the laser power also provides the additional benefit of limiting the power delivered in that the fiber or fibers can be arranged to transmit only a fraction of the laser output. This reduces the potential for damaging the chip 20 and/or board 21 being tested. Moreover, optical fibers contain the beam to prevent accidental exposure and precisely focus the laser beam energy upon an extremely small area on the chip's surface.

As known in the art, radiating a specimen surface with pulsed laser energy can generate broadband acoustic waves, mainly ultrasonic frequency waves. As the laser beam heats a small spot on the surface of the specimen, the local thermal expansion and contraction within the specimen generates stress waves. For low absorbed fluxes, the absorption surface does not exceed the melting temperature, so the ultrasonic source is a transient dilatation. The stress associated with this dilatation is, for the most part, below the elastic limit, and this mode of generation is referred to as thermoelastic. At high incident fluxes, however, the surface temperature rise is capable of exceeding the vaporization temperature. In such a situation, atoms leave the surface at high velocities imparting a momentum to the specimen surface. This mode of generation is referred to as ablation. Because electronic chips are delicate, ablation should be avoided to ensure that the chip is not damaged. Because larger chips require more energy to cause vibration, a linear fiber array may be used to create a simultaneous ultrasound generation at multiple points on the surface of a relatively large chip. By spreading the point source of ultrasound to several such points, the total power delivered to the chip 20 can be increased while maintaining safe, localized energy concentrations. The number of fibers in an array can be scaled to match the size of the chip, providing adequate power to induce motion without causing damage to the chip.

The positioning system 14 can take any one of several possible configurations. By way of example, the positioning system 14 can comprise a fixture which is capable of moving the chip 20 in both x and y directions such that discrete, predetermined points on the surface of the chip 20 can be sensed with the vibration sensing device 16. One arrangement particularly well-suited for the process development stage of a board assembly is a fixture which comprises first and second stepper motors 23 and 24. As is known in the art, such stepper motors 23, 24 are very precise instruments capable of very high resolution of movement. For instance, such stepper motors 23, 24 may have a position resolution of approximately 0.4 $\mu$m and a position accuracy of approximately 12 $\mu$m. This level of precision is deemed preferable especially where the size of the chip 20 is extremely small and therefore the various discrete points to be tested very close together. In the manufacturing context, the positioning system 14 can comprise an automated, indexed conveyor system (not shown) in which board assemblies can be tested with a predetermined frequency, e.g., one of every ten chips. In such an arrangement, the solder joint quality inspection system 10 of the present invention can be used to ensure quality control.

During testing of the manufactured boards, the ultrasonic vibrations created by the chip 20 in response to the ultrasound source 12 are sensed by the vibration sensing device 16. In a preferred arrangement, the vibration sensing device 16 comprises a laser interferometer. The vibration sensing device 16 records the surface displacement of the chip 20 as it vibrates up and down (i.e., in the z direction). When formed as a laser interferometer, the vibration sensing device 16 can comprise a fiber coupled head (not shown) for flexibility and positioning, and focusing optics (not shown) which allows the vibration sensing device 16 to be positioned remotely from the chip 20. Normally, the vibration sensing device 16 records data on a very broad bandwidth, for example 20 MHz, making it useful in a broad range of applications. Because the signals recorded from the vibration sensing device 16 can contain noise, especially when the device 16 is extremely sensitive, signal averaging and/or filtering may be necessary to produce clear signals. Typically, the vibration sensing device 16 will have a very high resolution such as approximately 0.25 nm, which allows for detection of very small differences in the vibration response.

Each of the ultrasound source 12, the positioning system 14, and the vibration sensing device 16 can be controlled by the system controller 18. Typically, the controller 18 activates the ultrasound source 12 so that it, for example, produces a pulsed laser beam of appropriate strength. In addition, the controller 18 can be used to adjust the positioning system 14 to correctly align the chip 20 with the vibration sensing device 16 so that readings can be taken. In a preferred arrangement, the system controller 18 comprises a computing device provided with appropriate execution software. As is discussed hereinafter, this controller 18 further can be used to process the data collected by the vibration sensing device 16 such that a determination can be made as to the quality of the solder joints used to secure the chip 20 to the board 21.

System Operation

With the system 10 described in the foregoing, solder joints, such as solder bumps or balls (as well as other types of solder joints), can be quality inspected. In addition, missing solder joints, improper chip registration, and the presence of surface defects each can be detected. In this testing, the ultrasound source 12 is used to excite the chip 20 into a vibration motion. During such vibration, the vibration sensing device 16 is used to measure the vibration displacement of the chip's surface. To aid in the detection and location of inferior solder joints, normally several such measurements are made at discrete, predetermined points of each chip 20. For instance, for a relatively small square chip, generally, one measurement reading can be taken in each of four quadrants of the chip 20 (see FIG. 2).

Figure 2:
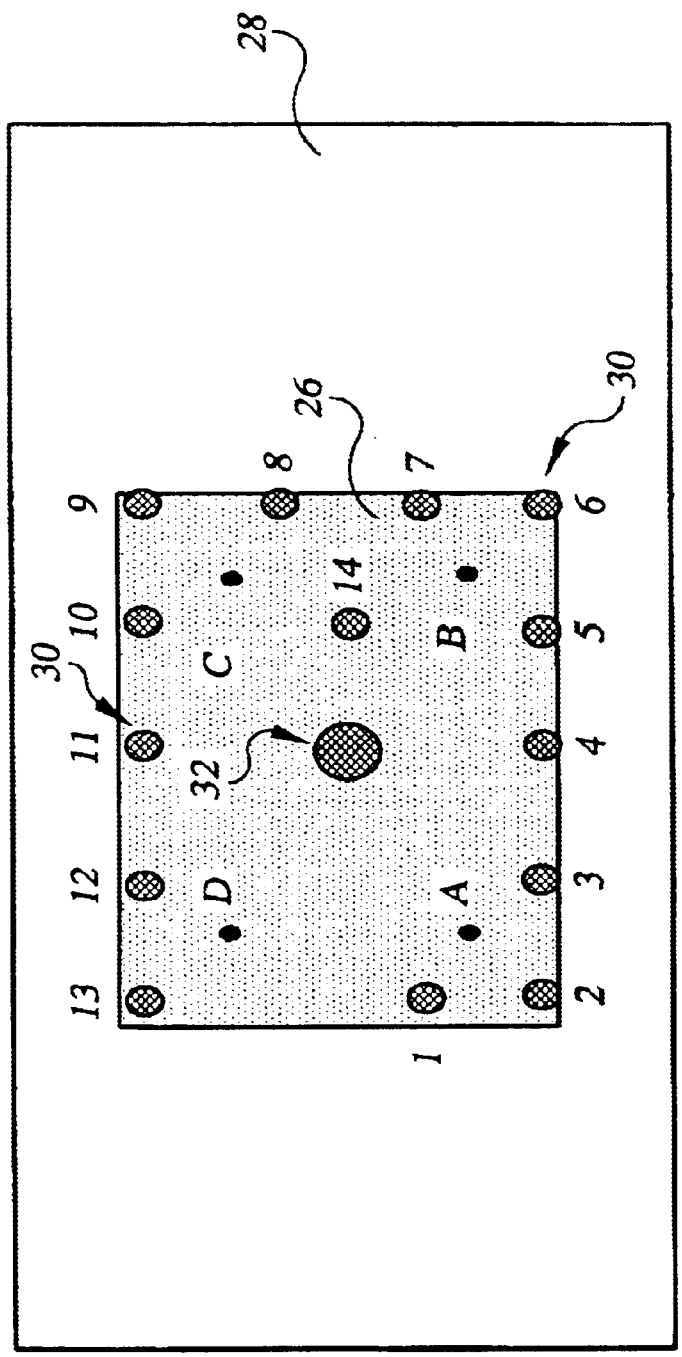
FIG. 2 is a schematic representation of a chip soldered to a board with a plurality of solder bumps which are to be tested in accordance with the present method.
Figure 3:
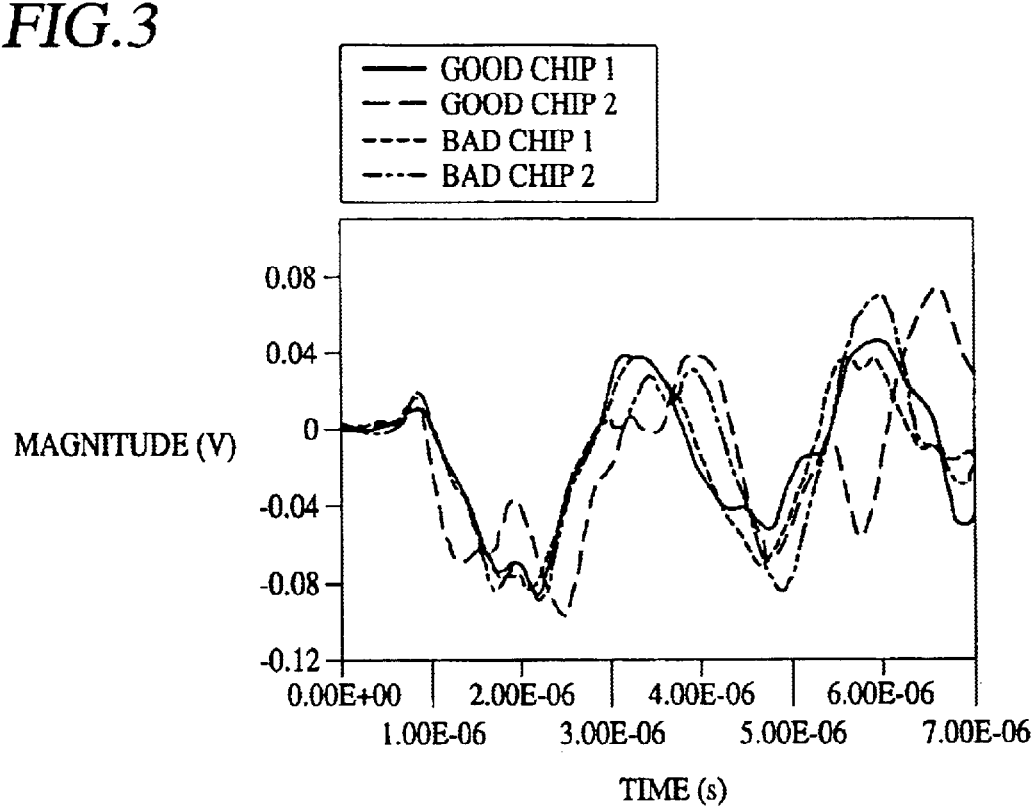
FIGS. 3–6 are plots of vibration displacement magnitude versus time of four different chips which were tested at four predetermined test points.
Figure 4:
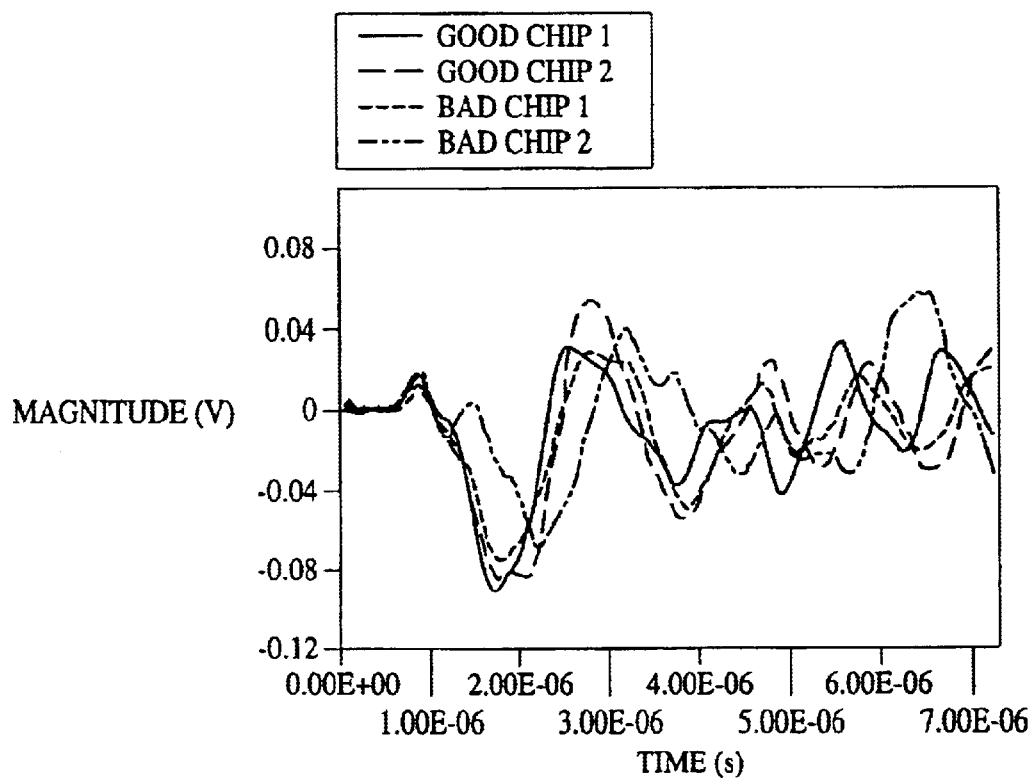
Figure 5:
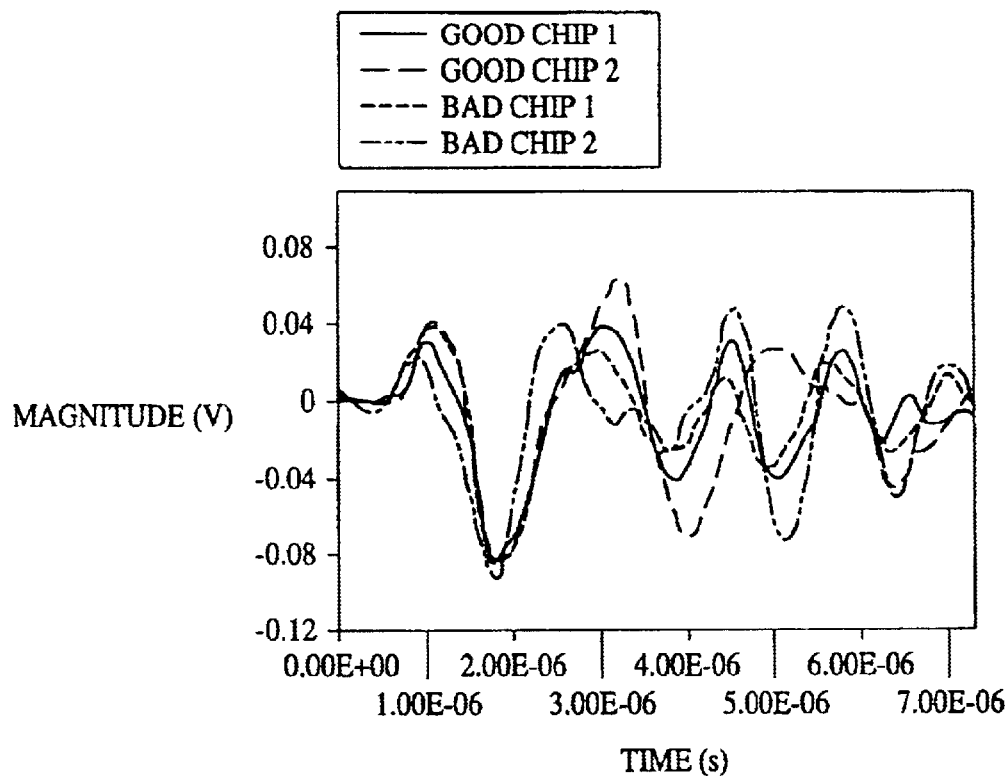
Figure 6:
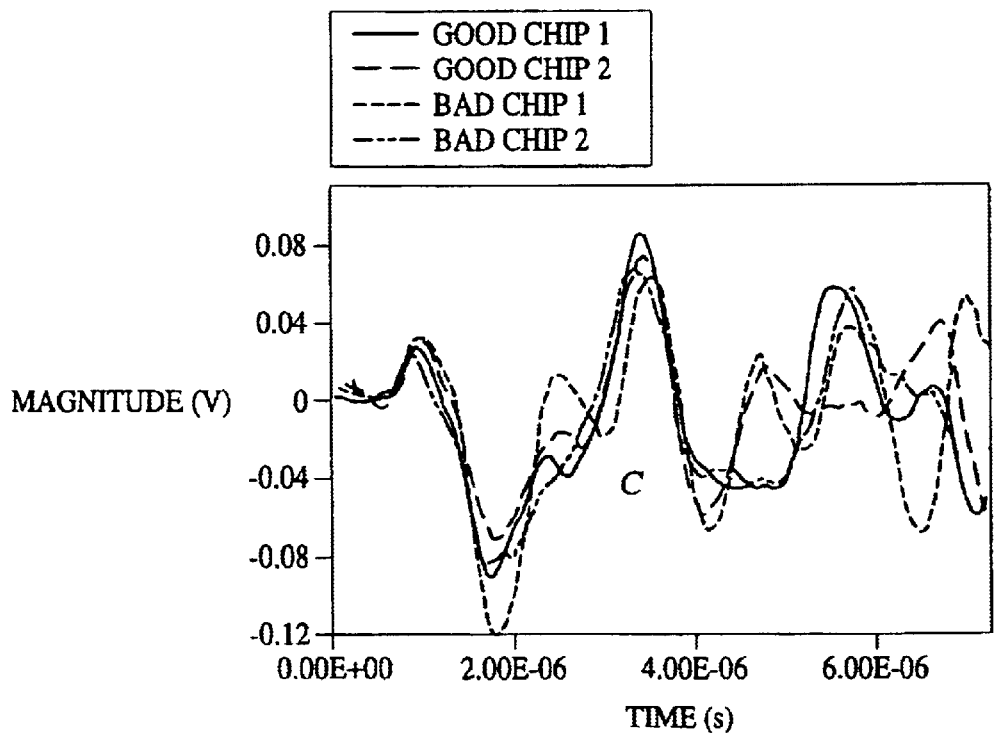

In that such measurements are meaningless without a reference point, the system 10 typically is calibrated so that the vibration response of a defective solder chip 20 can be detected. To conduct this calibration, a chip known to be non-defective is tested by measuring the vibration response of the chip at each of the selected test points. FIG. 2 illustrates such a non-defective chip 26 affixed to a board 28, such as a printed circuit board, with a plurality of solder bumps 30 which are disposed around the periphery of the chip 26 between the chip 26 and the board 28. As indicated in this figure, fourteen such solder bumps 30 are provided to hold and electrically connect the chip 26 to the board 28, each of these solder bumps 30 being identified with its own numeral. Assuming the chip 26 to be relatively small, that is only a few millimeters in width and length, the chip 26 can be excited to vibrate with a relatively small amount of laser light. Typically, as shown in FIG. 2, this incident laser light is trained on the chip 26 at a focal point 32 near the center of the chip 26. Where the chip 26 is relatively small, this incident laser light can be provided with, for instance, a single optical fiber which provides a single pulsed beam of light. Where the chip 26 is relatively large, however, for instance several centimeters wide and several centimeters long, several such optical fibers can be used to ensure that the appropriate degree of chip excitation is achieved. In such a case, several pulsed beams of laser light will be incident upon the chip surface. Normally, these beams will be gathered together in a grouping which, again, is focused near the center of the chip.

As laser light reaches the chip surface, the local thermal expansion and contraction generates stress waves in the chip 26 which, in turn, causes the chip 26 to vibrate toward and away from the vibration sensing device 16. As will be appreciated in the art, the magnitude of these vibrations will depend upon the quality of the solder joints holding the chip 26 in place on its board 28. Therefore, if one or more of these solder joints is disconnected or has internal voids, the magnitude of this displacement for a defective chip will be different from that observed with a chip having no defective solder joints.

As the vibration displacement is measured at the various discrete, predetermined points on the surface of the chip 26, the displacement magnitude at each test point is recorded so as to establish reference values for each point. With further reference to FIG. 2, a relatively small chip 26 can be measured at, for example, four discrete points such as points A, B, C, and D shown in FIG. 2. As indicated in this figure, each of these points A–D is located within a "quadrant" of the chip surface area. Arranged in this manner, a full picture of the vibration displacement of the chip 26 can be obtained. Once this information has been recorded, other chips of the same type can be tested in similar manner to observe how they compare to the reference chip.

FIGS. 3–6 are plots of the vibration responses of four different chips, two being non-defective ("good") and two being defective ("bad"), versus time taken at points A–D, respectively. As indicated in these plots, the vibration responses of each chip (at each point) are superimposed so that anomalous results can be easily identified. As is apparent from these figures, the defective chips have vibration response curves which are very different from those of the good chips. As is typically the case, defective chips have vibration displacements which are larger in magnitude than those of non-defective chips. Such a condition indicates a weak connection between the chip 26 and its board 28. If the chip being tested does have a solder joint defect, the effect of this defect will normally be noticeable across the entire surface of the chip. Accordingly, in the present example, the vibration response taken at each of points A–D will identify that the defect exists. As will be understood by persons having ordinary skill in the art, however, the difference in magnitude of the vibration displacement of a defective chip and a non-defective chip will be greatest at the measurement point which is closest to the location of the defect.

Although waveforms such as those illustrated in FIGS. 3–6 provide an indication of the existence or nonexistence of solder joint defects, the data collected by the vibration sensing device 16 can instead or in addition be processed in a manner in which the differences in vibration response can be more clearly quantified and compared. In a first processing method, the vibration response can be analyzed in the time domain. In a second processing method, the vibration response is analyzed in the frequency domain. In both methods, an automated comparison process is used to provide an estimate of the solder joint quality at each detection point. In the first method, a numerical algorithm is used to assign a value, called the error ratio, which represents solder quality of the tested chip at each detection point. The error ratio is a variable which measures the similarity of two waveforms in the time domain, and can be defined mathematically as $$Er = \frac{\int |f(t) - r(t)| dt}{\int r(t) dt}$$

where r(t) is the reference waveform and f(t) is the test waveform. As identified in the foregoing, a non-defective chip is used as the reference chip. Therefore, signals recorded from any other chip of the same type are compared with this reference chip. Because the absolute value of the error is used, the error ratio value will always be positive. Therefore, a signal that matches the reference signal well will have a small value, while a signal that has large changes in amplitude and phase will have a large value.

Figure 7:
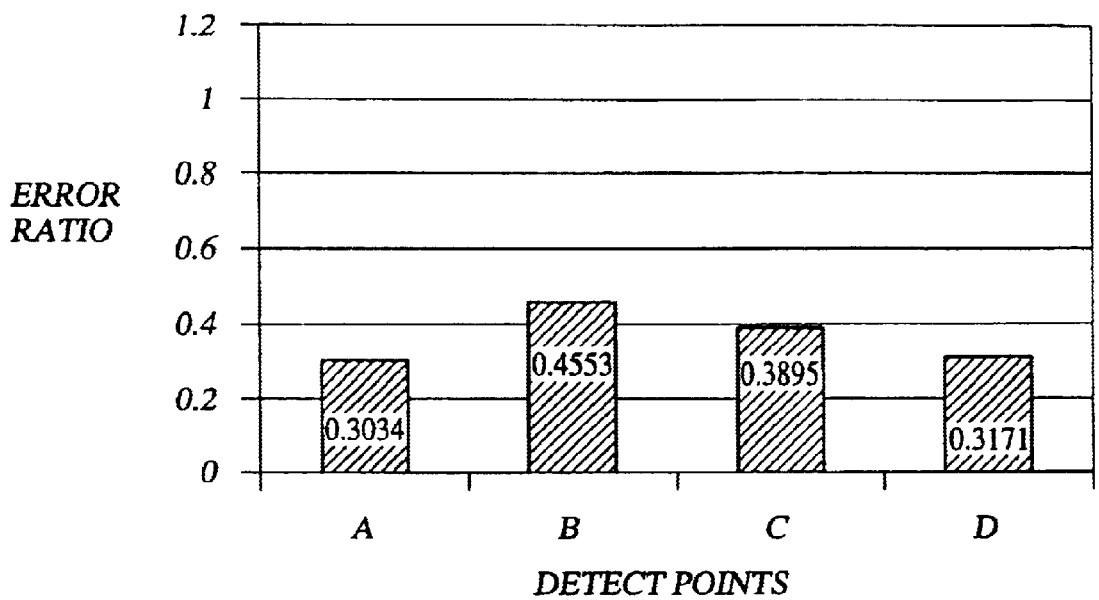
FIG. 7 is a graphical representation of the error ratios of an example non-defective chip.
Figure 8:
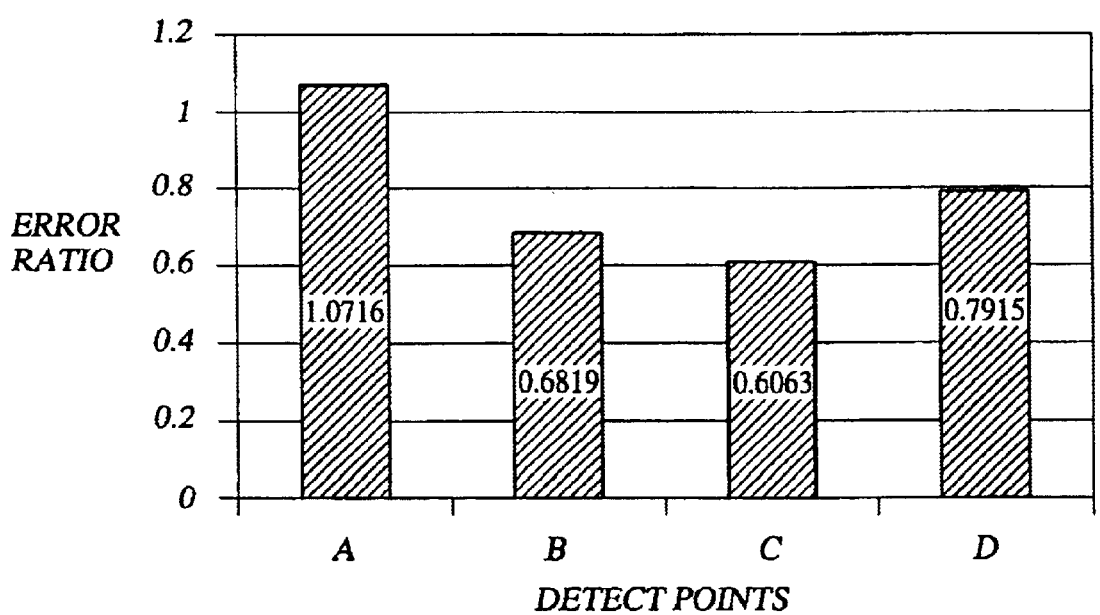
FIG. 8 is a graphical representation of the error ratios of an example defective chip.

Once these values have been calculated, the chip responses can be easily compared. For instance, as shown in FIGS. 7 and 8, the various error ratios for a non-defective chip and a defective chip, respectively, can be presented in graphical form. The graphs shown in FIGS. 7 and 8 clearly identify that the error ratios at the various test points of the defective chip are much larger those of the non-defective chip. Normally, a threshold value for the error ratio is established so that criteria can be established for deciding whether the tested chip is defective or acceptable. For instance, if the threshold value for error ratio is placed at 0.6, the vibration response of the chip in FIG. 8 would exceed the thresholds at each of the measuring points A–D. It can be therefore appreciated that error ratio analysis provides an automated method to obtain useful information as to solder joint integrity.

Figure 9:
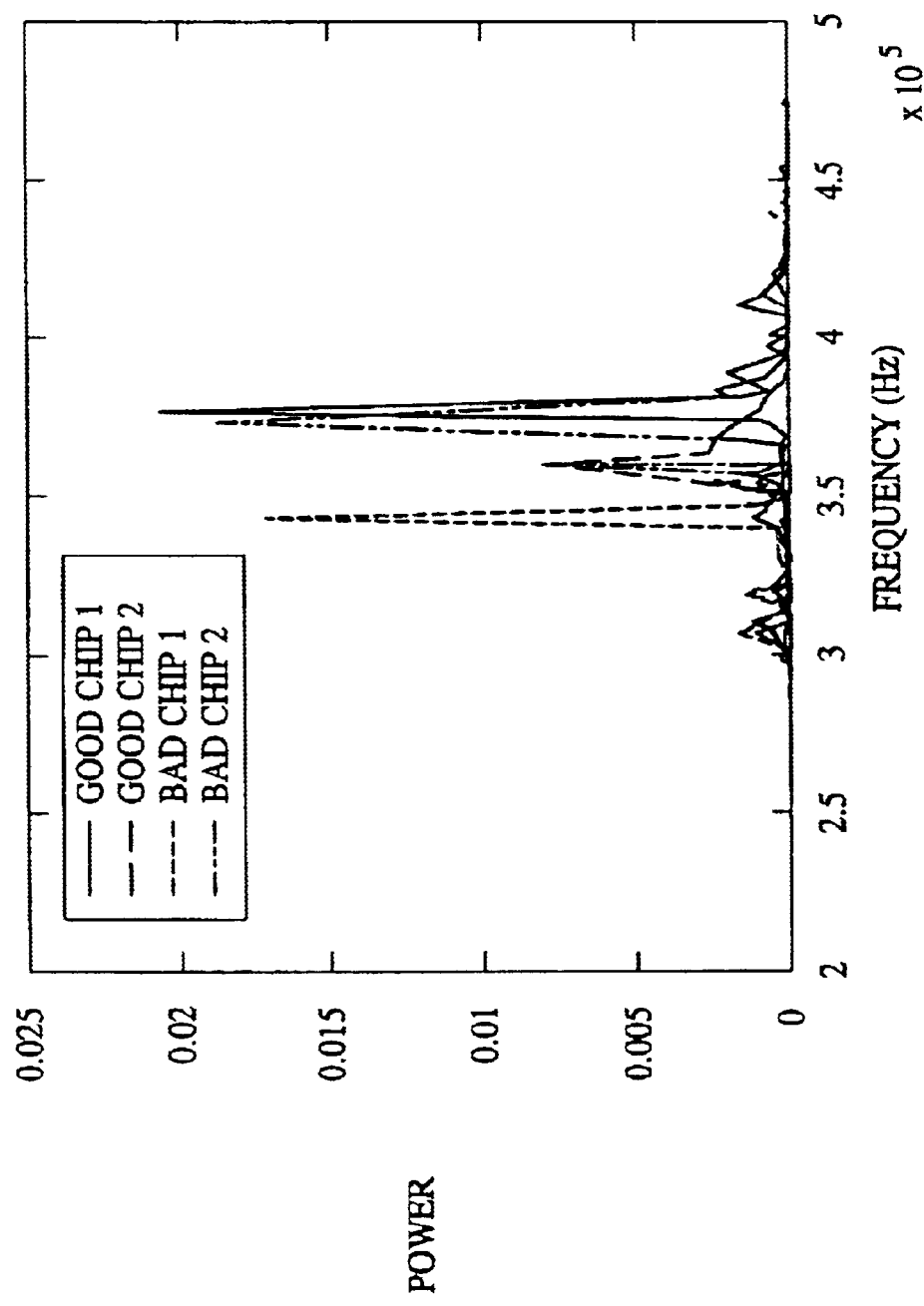
FIG. 9 is a plot comparing the frequency responses of four different chips.

In the second processing method, the vibration response is analyzed in the frequency domain. Such analysis is possible due to the fact that when a solder joint is missing or is defective, the stiffness of the support for the chip will change, causing the natural frequency of the chip to be altered. Because the acoustic wave generated by the pulsed laser is broadband, if the ultrasonic energy is strong enough, the vibration modes of the board can be excited and the chip will vibrate on its natural frequencies. In a preferred method, FFT techniques can be used to analyze the frequency distribution of vibration signals. The techniques for using FFT to analyze a function of time require that the time window in which the function is viewed to be sufficiently large to see the function decay to a relatively small value. In addition, sampling frequency must be considered, ensuring that it is large enough to avoid aliasing. FIG. 9 shows a frequency distribution of vibration signals detected at one particular detection point of four different chips, two of which being non-defective ("good") and two of which being defective ("bad"). By inspecting the frequency distribution shown in FIG. 9, and by performing vibration modal analysis based on finite element modeling, the first natural frequency of each chip can be calculated. In order to isolate other vibration modes and only consider the first mode, a band-passed digital filter (not shown) can be used having a passband from 300 KHz to 450 KHz. As is evident from FIG. 9, when the frequency distributions of good and bad chips are superimposed, the defective chips are easily distinguished from the non-defective chips.

In addition to using the testing data described herein to identify the existence and/or location of a defect, the system 10 of the present invention further can be used to determine the type of defect that is present. Although this information typically is not desired in that a defective chip is normally discarded regardless of the type of defect, identification of the defect type may be useful in the process development phase of a board assembly. To assess the type of defects encountered, the system 10 must be able to recognize the particular response that is associated with each particular defect. For instance, the vibration response obtained from a non-contacting solder bump is different from that obtained from a solder bump having an internal void. To get the system 10 to recognize and distinguish these various defects, a multiplicity of measurements of the various types of defects can be made by the system 10 so that a numerical range of phenomena, such as error ratios, can be established for each type of defect. Once these ranges have been established, each defect of each defective chip can be identified by type through comparison of its response data to the data collected previously as to the various types of defects. As will be appreciated in the art, confirmation of this identification can be made with conventional techniques such as those described in the background of this disclosure.

While particular embodiments of the invention have been disclosed in detail in the foregoing description and drawings for purposes of example, it will be understood by those skilled in the art that variations and modifications thereof can be made without departing from the spirit and scope of the invention as set forth in the following claims. For instance, when the system 10 is used in an industrial application, it may be desirable to filter environmental vibration noise after it is received by the vibration sensing device to calibrate the vibration sensing device to automatically reject such noise. Moreover, although the system 10 has been described herein as being used to detect solder joint defects, it will be appreciated that other defects, such as chip surface cracks, also can be detected in similar manner.

What is claimed is:

1. A method for inspecting an object, comprising:
    exciting the object with a pulsed laser beam such that the object vibrates, the pulsed laser beam being delivered to a surface of the object with at least one optical fiber;
    sensing the vibrations of the object to obtain vibration displacement data at a plurality of discrete, predetermined points of the object; and
    processing the vibration displacement data and comparing the data to vibration displacement data of a non-defective object to determine whether the object being tested is defective.

2. The method of claim 1, wherein the processing step comprises plotting vibration responses comprising vibration magnitude versus time of a reference object and the object being tested.

3. The method of claim 2, wherein the vibration responses are superimposed for comparison.

4. The method of claim 1, wherein the processing step comprises calculating an error ratio which is a numerical quantification of the quality of the object.

5. The method of claim 4, wherein the error ratio measures the similarity of the vibration response of a reference object and the object being tested.

6. The method of claim 3, wherein the error ratio is calculated by the equation:

$$Er = \frac{\int |f(t) - r(t)| dt}{\int r(t) dt}$$

where r(t) is the reference response and f(t) is the test response.

7. The method of claim 1, wherein the processing step comprises plotting frequency responses comprising vibration magnitude versus frequency of a reference object and the object being tested.

8. The method of claim 7, wherein the frequency responses are superimposed for comparison.

9. The method of claim 1, further comprising displacing the object to align the focal point of said laser interferometer to the various discrete, predetermined test points.

10. The method of claim 1, wherein the processing step comprises comparing the data of a defective chip to vibration displacement data of a non-defective chip to determine the type of defect that is present.

11. The method of claim 7, wherein the frequency responses are obtained using Fast Fourier Transform (FFT) techniques.

12. A solder joint inspection system for testing the integrity of a device including a computer chip connected to a printed circuit board with solder joints:

a laser capable of producing a pulsed laser beam used to excite the chip to be tested such that the chip vibrates;

at least one optical fiber optically connected to said laser and adapted to be positioned with its exit end in close proximity to a surface of the chip to be tested, said at least one optical fiber delivering at least a fraction of the pulsed laser beam to the chip;

a laser interferometer adapted to sense the vibration displacements created in the chip with said laser;

a system controller which receives the vibration data from said laser interferometer; and logic configured to process the vibration data such that it can be used to evaluate a type of defect present in the device.

13. The system of claim 12, wherein a plurality of optical fibers are optically connected to said laser and adapted to be positioned with their exit ends in close proximity to the surface of the chip to be tested, said optical fibers delivering the stimulus to the chip.

14. The system of claim 12, wherein said logic produces an error ratio which comprises a numerical quantification of the quality of the chip being tested.

15. The system of claim 12, further comprising a positioning system capable of adjusting the x and y positions of the chip being tested.

16. A solder joint inspection system for testing the integrity of solder joints used to connect a computer chip to a printed circuit board, comprising:

a laser capable of producing a pulsed laser beam used to excite the chip to be tested such that the chip vibrates;

at least one optical fiber optically connected to said laser and adapted to be positioned with its exit end in close proximity to a surface of the chip to be tested, said at least one optical fiber delivering at least a fraction of the pulsed laser beam to the chip;

a laser interferometer adapted to sense the vibration displacements created in the chip with said laser;

a system controller which receives the vibration data from said laser interferometer; and logic configured to process the vibration data such that it can be used to evaluate the integrity of the solder joints used to connect the chip to the printed circuit board.

17. The system of claim 16, wherein a plurality of optical fibers are optically connected to said laser and adapted to be positioned with their exit ends in close proximity to the surface of the chip to be tested, said optical fibers delivering the stimulus to the chip.

18. The system of claim 16, wherein said logic produces a vibration response curve which plots vibration magnitude versus time.

19. The system of claim 16, wherein said logic produces an error ratio which comprises a numerical quantification of the quality of the chip being tested.

20. The system of claim 16, wherein said logic produces a frequency response curve which plots vibration magnitude versus frequency.

21. The system of claim 16, further comprising a positioning system capable of adjusting the x and y positions of the chip being tested.

22. The system of claim 16, wherein said system controller comprises a computing device having appropriate executing software.

23. The system of claim 16, wherein operation of said laser and said laser interferometer is controlled by said system controller.

24. The system of claim 16, wherein a plurality of optical fibers are optically connected to said laser and adapted to be positioned with their exit ends in close proximity to the surface of the chip to be tested, said optical fibers delivering the pulsed laser beam to the chip.

25. The system of claim 16, further comprising a positioning system capable of adjusting the x and y positions of the chip being tested.

26. The system of claim 25, wherein said positioning system comprises an x direction stepper motor and a y direction stepper motor.

27. The system of claim 25, wherein operation of said positioning system is controlled by said system controller.

* * * * *